(12) United States Patent
Chance et al.

(10) Patent No.: US 9,599,623 B2
(45) Date of Patent: Mar. 21, 2017

(54) DIAGNOSTIC DEVICES, METHODS AND SYSTEMS FOR DETECTING PLATELET FACTOR 4 (PF4)/HEPARIN ANTIBODIES

(75) Inventors: Suzette Chance, Richfield, WI (US); Gian Paolo Visentin, Waukesha, WI (US)

(73) Assignee: IMMUCOR GTI DIAGNOSTICS, INC., Waukesha, WI (US)

(*) Notice: Subject to any disclaimer, the term of this patent is extended or adjusted under 35 U.S.C. 154(b) by 43 days.

(21) Appl. No.: 14/124,533

(22) PCT Filed: Jun. 5, 2012

(86) PCT No.: PCT/US2012/040938
§ 371 (c)(1),
(2), (4) Date: Oct. 6, 2014

(87) PCT Pub. No.: WO2012/170435
PCT Pub. Date: Dec. 13, 2012

(65) Prior Publication Data
US 2015/0064800 A1    Mar. 5, 2015

(51) Int. Cl.
*G01N 33/558* (2006.01)
*G01N 33/68* (2006.01)
*G01N 33/86* (2006.01)

(52) U.S. Cl.
CPC ....... *G01N 33/6854* (2013.01); *G01N 33/558* (2013.01); *G01N 33/6863* (2013.01); *G01N 33/86* (2013.01); *G01N 2800/32* (2013.01)

(58) Field of Classification Search
CPC .. G01N 33/6854; G01N 33/558; G01N 33/86; G01N 33/6863
See application file for complete search history.

(56) References Cited

U.S. PATENT DOCUMENTS

| | | | |
|---|---|---|---|
| 4,981,786 A * | 1/1991 | Dafforn | G01N 33/5302 422/412 |
| 7,871,781 B2 * | 1/2011 | Rundstrom | G01N 33/543 422/423 |
| 2001/0041339 A1 * | 11/2001 | Anderson | B01J 19/0046 435/6.11 |
| 2006/0128029 A1 * | 6/2006 | Goerlach-Graw | G01N 33/558 436/514 |
| 2006/0166374 A1 * | 7/2006 | Hubscher | G01N 33/558 436/514 |
| 2010/0112628 A1 * | 5/2010 | Gernez | G01N 33/5094 435/29 |
| 2010/0255510 A1 * | 10/2010 | Wang | G01N 33/86 435/7.25 |

* cited by examiner

*Primary Examiner* — Melanie Y Brown
(74) *Attorney, Agent, or Firm* — Mintz Levin Cohn Ferris Glovsky and Popeo, P.C.

(57) ABSTRACT

The present invention provides a novel assay for detecting human antibodies specific for a platelet factor 4 (PF4)/heparin complex in a fluid sample. The assay utilizes an immobilized PF4/polyanion complex and an anti-human antibody conjugated to a non-particulate fluorescent dye to capture and detect human PF4/heparin antibodies. Various devices, methods and systems based on the disclosed PF4/heparin assay are also provided.

11 Claims, 7 Drawing Sheets

DIAGNOSTIC DEVICES, METHODS AND SYSTEMS FOR DETECTING PLATELET FACTOR 4 (PF4)/HEPARIN ANTIBODIES

CROSS-REFERENCE TO RELATED APPLICATIONS

This application is a national phase filing under 35 U.S.C. §371 of International Application No. PCT/US2012/040398 filed Jun. 5, 2012, which claims priority under 35 U.S.C. §119(e) to provisional patent application Ser. No. 61/495,171 filed Jun. 9, 2011, the disclosures of which are hereby incorporated by reference in their entirety.

FIELD OF THE INVENTION

This invention generally relates to the field of immunodiagnostics. More specifically, the invention relates to the detection of antibodies against the platelet factor 4 (PF4, also known as C—X—C motif chemokine ligand 4 or CXCL4) and heparin complex, which are associated with heparin-induced thrombocytopenia (HIT). In particular, the invention provides novel lateral flow assay devices, methods and systems for detecting antibodies specific for PF4/heparin or PF4/polyanion complexes in fluid samples.

BACKGROUND OF THE INVENTION

Heparin-induced thrombocytopenia (HIT), the most frequent drug-induced immune-mediated type of thrombocytopenia (low platelet level in the blood), is an important and sometimes life-threatening complication of heparin therapy. Heparin is the most widely used intravenous anti-coagulant and one of the most widely prescribed drugs in the U.S. More than one trillion units are administered annually to approximately 12 million patients. Intravenous heparin is commonly used for the prophylaxis and treatment of thromboembolic disease, as well as numerous other applications including certain types of heart and lung disorders, and during or after a variety of surgery including open heart, bypass, dialysis and orthopedic procedures. Heparin is also used for diagnostic and therapeutic interventional radiologic procedures. HIT can be triggered by standard therapeutic dose heparin, low-dose (prophylactic treatment), low molecular weight heparin, unfractionated heparin and even by minute quantities given to flush intravascular catheters.

HIT is classified into Type I and Type II, Type I being benign and Type II severe. Type I occurs early after heparin initiation, when the platelet levels are reduced only slightly and usually return to normal even if heparin treatment is continued. Thromboembolic complications are rare, and Type I HIT is not antibody-mediated.

In contrast, Type II HIT is a clinicopathologic syndrome caused by platelet activating antibodies that recognize complexes of platelet factor 4 (PF4) and heparin (PF4/heparin) (Amiral et al., Thromb. Haemost. 1992, 68:95-96). Thrombocytopenia occurring within 5-14 days of administration of heparin is the most common clinical effect. The most severe complication of HIT is the occurrence of venous and arterial thrombosis (HIT-associated thrombosis or HITT). Venous thrombosis can result in limb gangrene and the need for limb amputation. Other symptoms of Type II HIT may include cutaneous reactions, from a simple allergic reaction to lesions and necrosis.

The basic pathogenesis of HIT is reasonably well characterized. Upon exposure to exogenous heparin, multimolecular complexes composed of PF4 and heparin form. The binding of PF4 to heparin in these complexes is associated with a conformational change in PF4, exposing a neoepitope (Reilly, Semin. Dial. 2003, 16:54-60). The present inventors previously reported that many polyanionic compounds other than heparin (e.g., polyanions such as polyvinyl sulfonate) can form complexes with PF4 and cause similar conformation change in the molecule (Visentin et al., J. Lab. Clin. Med. 2001, 138:22-31; U.S. Pat. No. 5,972,718, incorporated herein by reference). This heparin-dependent neoepitope elicits an immune response in some patients; the antibody response is usually an IgG type of antibody, although IgA and IgM types have also been implicated (Amiral et al., Br. J. Haematol. 1996, 92:954-59). The antibody binds to the PF4/heparin complex, creating an immune complex that binds to immunoglobulin receptors on the platelet surface (FcγRIIA or CD32). Aggregation of FcγRIIA receptors by the immune complex triggers platelet activation and aggregation through transmembrane signaling. In addition, during the process of platelet activation, platelets release phospholipid microparticles derived from the cell membrane. These microparticles support the enzymatic reactions of the coagulation cascade, leading to thrombin formation; consequently, the release of these microparticles into the circulation is thrombogenic. Further, the PF4/heparin immune complexes can bind to glycosaminoglycans on the endothelium, leading to endothelial injury. The endothelial damage may also participate in the "thrombotic storm" associated with this syndrome.

Early diagnosis of HIT is essential to reduce morbidity and mortality. The diagnosis of HIT is usually based on clinical abnormalities including thrombocytopenia with or without thrombosis and the detection of antibodies to the PF4/heparin complex (termed PF4/heparin antibodies). There are two major types of assays for the detection of heparin dependant antibodies: functional assays and PF4-dependent antigen immunoassays. Functional assays include the serotonin release assay (SRA; Sheridan et al., Blood 1986, 67:27-30), the platelet aggregation assay (Chong et al., Thromb. Haemost. 1993, 69:344-50) and the heparin-induced platelet activation (HIPA) assay (Greinacher et al., Thromb. Haemost. 1991, 66:734-36). Functional assays are technically difficult to perform and are considered to be complex specialty assays.

Enzyme linked immunoassays (ELISAs) are the most frequently used PF4-dependent antigen immunoassay (Greinacher et al., Hematol. 1994, 34:381-85; Visentin et al., J. Clin. Invest. 1994, 93:81-88; see also U.S. Pat. Nos. 5,466,582, 5,972,717, 5,972,718, 6,964,854, 7,011,953 and 7,728,115; U.S. Patent Application Pub. No. 2010/0015647; and Int'l Pub. No. WO 2010/024271, all of which are incorporated herein by reference). Commercially available ELISAs for the detection of PF4/heparin antibodies include PF4 IgG™ and PF4 Enhanced® (both from Gen-Probe GTI Diagnostics, Waukesha, Wis.); Asserachrom® HPIA and Asserachrom® HPIA-IgG (both from Diagnostica Stago, Asnières, France); Technozym® HIT IgG (Technoclone, Vienna, Austria); and Zymutest HIA IgGAM (Hyphen Biomed, Neuville, France). ELISAs, while not particularly complex, are generally not available on a point-of-care basis.

Although HIT is a true clinicopathologic syndrome, its diagnosis still rests primarily on clinical grounds since laboratory tests may not be available locally or may not be available in a sufficiently timely manner. Owing to the high risk of HIT-associated thrombosis, antithrombotic therapy with alternative anticoagulants should be started immediately when serologic assays confirm clinical suspicion.

Readily available results, obtained from immunoassays for rapid detection of PF4/heparin antibodies, may be combined with the pretest estimation of clinical probability in order to exclude and/or confirm the diagnosis of HIT, thereby assisting physicians in the time-sensitive clinical management of HIT.

A number of rapid PF4-dependent antigen immunoassays have been described, e.g., the particle immunofiltration assay (PIFA) disclosed in U.S. Patent Application Pub. No. 2006/0172438 and corresponding Int'l Pub. No. WO 2006/042089, as well as the lateral flow immunoassay (LFIA) disclosed in and U.S. Patent Application Pub. No. 2010/0255510 and corresponding Int'l Pub. No. WO 2009/111254, all incorporated herein by reference. Several rapid PF4-based immunoassays have been developed commercially. ID-PaGIA Heparin/PF4 Antibody Test (DiaMed/Bio-Rad, Cressier, Switzerland) is a rapid particle gel immunoassay that utilizes PF4 coated onto synthetic polymer particles. PIFA® Heparin/PF4 Rapid Assay (Akers Biosciences, Thorofare, N.J.) is a particle immunofiltration assay that uses dyed microparticles coated with purified PF4 protein. Enhancing agents promote rapid matrix formation of these microparticles in the presence of PF4/heparin antibodies, and visual color results are produced through the interaction of these microparticles with a membrane-filtration system. Finally, Milena® QuickLine HIT (Milenia Biotec, Gießen, Germany) is a rapid lateral flow immunoassay wherein goat anti-human IgG antibodies immobilized on the nitrocellulose membrane bind human IgG antibodies previously captured by a PF4/polyanion complex which is detected using intensely colored gold nanoparticles.

Despite the commercial availability of various PF4-dependent antigen immunoassays, there remains a significant need for simple, rapid, sensitive and specific methods for detecting PF4/heparin antibodies in fluid samples, particularly ones that can be performed in the point-of-care settings without relying on sophisticated laboratory equipment. The present invention addresses this need.

SUMMARY OF THE INVENTION

In one aspect, the invention provides a device for detecting the presence of human platelet factor 4 (PF4)/heparin antibodies in a fluid sample, such as a blood sample. The device includes a PF4/polyanion complex immobilized on a solid support and an anti-human antibody labeled with a non-particulate fluorescent dye. In some embodiments, the device is a lateral flow device, and the solid support is a test strip. In preferred embodiments, the labeled anti-human antibody is releasably attached to the test strip upstream of the immobilized PF4/polyanion complex.

In another aspect, the invention provides a method for detecting the presence of human heparin/platelet factor 4 (PF4) antibodies in a fluid sample, such as a blood sample. The method includes forming a sandwich complex comprising a PF4/polyanion complex immobilized on a solid support, PF4/heparin antibodies, and an anti-human antibody labeled with a non-particulate fluorescent dye. In some embodiments, the sandwich complex is formed in a lateral flow format, such that the solid support is a test strip. The labeled anti-human antibody is preferably contacted with the PF4/heparin antibodies only after the PF4/heparin antibodies have bound to the immobilized PF4/polyanion complex.

The numerous technical advantages of using an immobilized PF4/polyanion complex instead of an immobilized PF4/heparin complex for PF4/heparin antibody capture are discussed in detail in U.S. Pat. No. 5,972,718, which discussion is incorporated herein by reference. Further, the device and method described herein provide superior assay performance by virtue of employing non-particulate fluorescent labels, which is contrary to the popular practice of using particulate labels for lateral flow detection. This design feature addresses the strongly negative charge profile of the immobilized PF4/polyanion complex. In the course of development, the inventors found that positively charged latex particles tend to aggregate and bind non-specifically to the negatively charged polyanion. Although neutrally charged gold particles do not have the specificity problem, they provide a very limited dynamic range for the purposes of detecting PF4/heparin antibodies. The present inventors subsequently discovered that non-particulate fluorescent labels, particularly those without a significant positive charge, provide an excellent dynamic range while demonstrating minimal non-specific binding to the PF4/polyanion complex.

In the above aspects of the invention, the polyanion is preferably selected from the group consisting of polyvinyl sulfonate, polystyrene sulfonate, polyanetholesulfonate, polyvinyl phosphate, polyvinyl phosphonate, polyvinyl sulfate, and a combination thereof. In particularly preferred embodiments, the polyanion is polyvinyl sulfonate (PVS). The labeled anti-human antibodies are preferably selected from the group consisting of antibodies specific for IgG, IgA, IgM, and a combination thereof. In some embodiments, the labeled antibodies comprise a mixture of antibodies specific for IgG, IgA and IgM. In other embodiments, the labeled antibodies comprise antibodies specific for IgG only. In preferred embodiments, the labeled antibodies are goat anti-human antibodies. The non-particulate fluorescent label preferably comprises an amine-reactive dye, such as a DyLight™ an Alexa Fluor®, a HiLyte Fluor™, a CyDye™, a Cy®, a CF™, an IRDye®, or a combination thereof.

In a further aspect, the invention provides a lateral flow assay device for detecting the presence of human platelet factor 4 (PF4)/heparin antibodies in a fluid sample, such as a blood sample. The device comprises a test strip which includes a conjugate pad and a porous membrane positioned downstream of, and in fluid communication with, the conjugate pad. The conjugate pad includes a conjugate zone, a sample zone, and a sample buffer zone. The conjugate zone contains anti-human antibodies, e.g., goat anti-human immunoglobulins, releasably attached thereto and labeled with a non-particulate fluorescent dye, e.g., an amine-reactive dye. The sample zone is positioned downstream of the conjugate zone and configured to receive a fluid sample, such as a whole blood, serum or plasma sample. The sample buffer zone is positioned intermediate to the conjugate zone and the sample zone and configured to receive a sample buffer that facilitates lateral transport of the fluid sample. The porous membrane is positioned downstream of, and in fluid communication with, the conjugate pad and includes a detection zone and a control zone. The detection zone contains a PF4/polyanion complex immobilized thereon. The control zone is positioned downstream of the detection zone and contains a capture reagent, e.g., mouse anti-goat immunoglobulins, immobilized thereon and configured to bind with the labeled anti-human antibodies.

In this aspect of the invention, the conjugate pad may further include a conjugate buffer zone positioned upstream of the conjugate zone and configured to receive a conjugate buffer that solubilizes the labeled anti-human antibodies and facilitates their lateral transport. In other embodiments, the conjugate buffer zone may reside on a separate pad, herein referred to as a "wet pad," which is positioned upstream of, and in fluid communication with, the conjugate pad. In preferred embodiments, the test strip may also include a wicking pad in fluid communication with the porous membrane, such that the membrane is positioned intermediate to the conjugate pad and the wicking pad. The purpose of the wicking pad is to enhance lateral transport by withdrawing fluid from the porous membrane. Although the conjugate pad is preferably embodied in a single integral pad, it is further contemplated that the conjugate pad may include a discrete conjugate portion, containing the conjugate zone, and a discrete sample portion, containing the sample zone and the sample buffer zone, such that the conjugate and sample portions are in fluid communication with each other.

In addition to its use of a non-particulate fluorescent label in combination with an immobilized PF4/polyanion complex, the lateral flow assay configuration described herein has a further advantageous design feature that provides superior assay performance. Namely, the conjugate zone containing the labeled anti-human antibody is located upstream of the sample zone and sample buffer zone. This is contrary to the conventional lateral flow assay arrangement, wherein the conjugate zone is positioned downstream of the sample zone and/or sample buffer zone in order to solubilize the detection label and bind it to an analyte of interest as the analyte flows through the conjugate zone.

This design feature addresses a problem caused by the fact that the typical sample to be tested is blood, plasma or serum that includes a mixture of immunoglobulins, most which are not specific for PF4/heparin. Given that the conjugate used in this assay comprises generic anti-human antibodies, e.g., goat anti-human immunoglobulins, there is an enormous potential for non-specific binding between the conjugate and non-PF4/heparin antibodies in the sample, resulting in the depletion of conjugate available for binding with PF4/heparin antibodies. Therefore, it is crucial for the conjugate not to come in contact with the sample until the sample has traveled through the detection zone, and the PF4/heparin antibodies in the sample have bound to the immobilized PF4/polyanion complex. The device configuration disclosed herein satisfies this requirement by reversing the conventional positions of the sample zone and conjugate zone, thereby completely dissociating the transport of the labeled anti-human antibodies from the sample transport.

In preferred embodiments, the test strip is affixed to a solid backing and enclosed in a cassette, e.g., a plastic cassette. Typically, the cassette includes a first opening configured to expose the sample zone and a second opening configured to expose the detection zone and the control zone. It will be appreciated that access to the sample zone is required in order to apply the fluid sample to the assay device. It will also be appreciated that access to the detection and control zones is needed in order to detect fluorescent signals. In some embodiments, the cassette may also include a third opening configured to expose the sample buffer zone and/or a fourth opening configured to expose the conjugate buffer zone. In these embodiments, access to the sample buffer and conjugate buffer zones is desirable for applying the sample and conjugate buffers to the sample and conjugate zones, respectively.

In certain alternative embodiments, the assay device may further comprise a first buffer pouch configured to provide a sample buffer to the sample buffer zone and/or a conjugate buffer pouch configured to provide a conjugate buffer to the conjugate buffer zone. In these embodiments, the device preferably includes means for releasing the sample buffer and/or the conjugate buffer when a positive pressure is applied to the sample buffer pouch and/or the conjugate buffer pouch. The releasing means typically include blisters made of a flexible material and covering the sample buffer pouch and/or conjugate buffer pouch, and optionally further include a piercing member, e.g., a pin or a tack, configured and adapted to break the sample buffer pouch and/or the conjugate buffer pouch when a positive pressure is applied to the blisters. In some embodiments, the assay device described herein further includes a radio-frequency identification (RFID) chip containing one or more assay parameters and/or lot information (e.g., product name, lot number, expiration date etc.).

The conjugate pad may be made of polyester, whereas the porous membrane may be made of nitrocellulose. In some embodiments, the wet pad is made of polyester, whereas the wicking pad is made of a cellulose material having a sufficiently strong capillary action. The polyanion is preferably selected from the group consisting of polyvinyl sulfonate, polystyrene sulfonate, polyanetholesulfonate, polyvinyl phosphate, polyvinyl phosphonate, polyvinyl sulfate, and a combination thereof. In particularly preferred embodiments, the polyanion is polyvinyl sulfonate (PVS). The labeled anti-human antibodies are preferably selected from the group consisting of antibodies specific for IgG, IgA, IgM, and a combination thereof. In some embodiments, the labeled antibodies comprise a mixture of antibodies specific for IgG, IgA and IgM. In other embodiments, the labeled antibodies comprise antibodies specific for IgG only. In preferred embodiments, the labeled antibodies are goat anti-human antibodies. The non-particulate fluorescent label preferably comprises an amine-reactive dye, such as a DyLight™, an Alexa Fluor®, a HiLyte Fluor™, a CyDye™, a Cy®, a CF™, an IRDye®, or a combination thereof. The capture reagent preferably binds to immunoglobulins from the mammalian species used to generate the anti-human antibodies for the conjugate. For example, if the anti-human antibodies are raised in goat, the capture reagent may comprise an anti-goat antibody, such as a mouse anti-goat antibody.

In another aspect, the invention provides a method for detecting the presence of human PF4/heparin antibodies in a fluid sample, such as a blood sample. The method includes the following steps: a) obtaining a lateral flow assay device according to the present invention; b) contacting a sample containing or suspected of containing PF4/heparin antibodies with the sample zone; c) transporting PF4/heparin antibodies, if present in the sample, to the detection zone to bind with the immobilized PF4/polyanion complex, thereby immobilizing the PF4/heparin antibodies in the detection zone; d) subsequent to step c), transporting the anti-human antibodies labeled with the non-particulate fluorescent dye to the detection zone to bind with the immobilized PF4/heparin antibodies, thereby immobilizing the labeled anti-human antibodies in the detection zone; e) transporting unbound labeled anti-human antibodies to the control zone to bind with the immobilized capture reagent, thereby immobilizing the labeled anti-human antibodies in the control zone; and f) assessing fluorescence from the non-particulate fluorescent label in the detection and control zones, wherein the presence of fluorescence in both of said zones is indicative of the presence of PF4/heparin antibodies in the sample.

In this aspect of the invention, the step of transporting PF4/heparin antibodies to the detection zone includes applying a sample buffer to the sample buffer zone to facilitate lateral transport. In preferred embodiments, the sample buffer comprises 1× phosphate buffered saline (PBS), bovine serum albumin (BSA) and polysorbate 20 (Tween 20™). The concentration of BSA is preferably about 1%, and the concentration of Tween 20™ is preferably about 0.1%. The pH of the sample buffer is preferably adjusted to about 7.4.

In some embodiments, the step of transporting the anti-human antibodies labeled with the non-particulate fluorescent dye to the detection zone includes applying a conjugate buffer to the conjugate buffer zone to solubilize the labeled anti-human antibodies and facilitate their lateral transport. The composition of the conjugate buffer may be the same as or different than the composition of the sample buffer. In preferred embodiments, the conjugate buffer comprises 1×PBS, BSA and Tween 20™. The concentration of BSA is preferably about 1%, and the concentration of Tween 20™ is preferably about 0.1%. The pH of the conjugate buffer is preferably adjusted to about 7.4.

As noted above, the polyanion is preferably selected from the group consisting of polyvinyl sulfonate, polystyrene sulfonate, polyanetholesulfonate, polyvinyl phosphate, polyvinyl phosphonate, polyvinyl sulfate, and a combination thereof. In particularly preferred embodiments, the polyanion is polyvinyl sulfonate (PVS). The labeled anti-human antibodies are preferably selected from the group consisting of antibodies specific for IgG, IgA, IgM, and a combination thereof. In some embodiments, the labeled antibodies comprise a mixture of antibodies specific for IgG, IgA and IgM. In other embodiments, the labeled antibodies comprise antibodies specific for IgG only. In preferred embodiments, the labeled antibodies are goat anti-human antibodies. The non-particulate fluorescent label preferably comprises an amine-reactive dye, such as a DyLight™, an Alexa Fluor®, a HiLyte Fluor™, a CyDye™, a Cy®, a CF™, an IRDye®, or a combination thereof. The immobilized capture reagent is preferably an antibody that binds to immunoglobulins from the mammalian species used to generate the anti-human antibodies for the conjugate. For example, if the anti-human antibodies are raised in goat, the capture reagent may comprise an anti-goat antibody, such as a mouse anti-goat IgG.

In certain embodiments the method described herein further includes a step of transmitting at least one assay parameter and/or lot information (e.g., product name, lot number, expiration date etc.) using a radio-frequency identification (RFID) chip. In some particularly preferred embodiments, the assessing step comprises using a fluorometer to measure fluorescence in the detection and control zones.

In yet another aspect, the invention provides a point-of-care lateral flow immunoassay system for determining the presence and/or quantity of PF4/heparin complex induced immunoglobulin antibodies in a body fluid of a patient. The system includes a linear membrane of an inert, fibrous material capable of supporting a movement of liquids by capillary action and which in turn, is supported by a backing; a means for binding a light absorbing label to PF4/heparin complex induced immunoglobulin antibodies present in a sample of the body fluid passing through the conjugate/sample pad; and a means for immobilizing on the membrane in the detection zone, a PF4/polyanion complex. The linear membrane is zoned, from proximal end to distal end, into a conjugate zone, a sample pad, a detection zone, a control zone, and a wicking pad, each optionally separated from its adjacent zone by a flow zone. The PF4/polyanion complex is capable of conjugatively binding to PF4/heparin complex induced immunoglobulin antibodies bound to the light absorbing label passing into the detection zone, wherein the light absorbing label facilitates the visibility of antibodies bound to the PF4/polyanion complex immobilized in the detection zone.

In this aspect of the invention, the body fluid may be blood or an immunoglobulin-containing component thereof, such as plasma or serum. The polyanion is preferably selected from the group consisting of polyvinyl sulfonate, polystyrene sulfonate, polyanetholesulfonate, polyvinyl phosphate, polyvinyl phosphonate, polyvinyl sulfate, and a combination thereof. In particularly preferred embodiments, the polyanion is polyvinyl sulfonate (PVS). In some embodiments, the PF4/heparin complex induced immunoglobulin antibodies are selected from the group consisting of IgG, IgA, IgE, IgM, and a combination thereof. In certain preferred embodiments, the light absorbing label is a fluorescent label, and the visibility of the antibodies is facilitated by an electro-optical reading device, such as a fluorometer.

BRIEF DESCRIPTION OF THE DRAWINGS

FIG. 1A illustrates the principle of analyte detection, whereas FIG. 1B shows a perspective view of an exemplary assay device.

FIG. 2A shows the top and side views of a basic configuration wherein the test strip includes an integral conjugate/sample pad, a porous membrane, and a wicking pad. FIG. 2B shows the top and side views of a modified configuration wherein the test strip includes a discrete wet pad, an integral conjugate/sample pad, a porous membrane, and a wicking pad. FIG. 2C shows the top and side views of a configuration wherein the test strip includes discrete conjugate and sample pads, a porous membrane, and a wicking pad.

FIG. 3A shows a perspective view of the device, wherein the sample and conjugate buffers are contained in blisters/pouches and released to the test strip when the blisters/pouched are compressed. FIG. 3B is a cross-section of the device shown in FIG. 3A.

DETAILED DESCRIPTION OF THE INVENTION

Figure 1A:
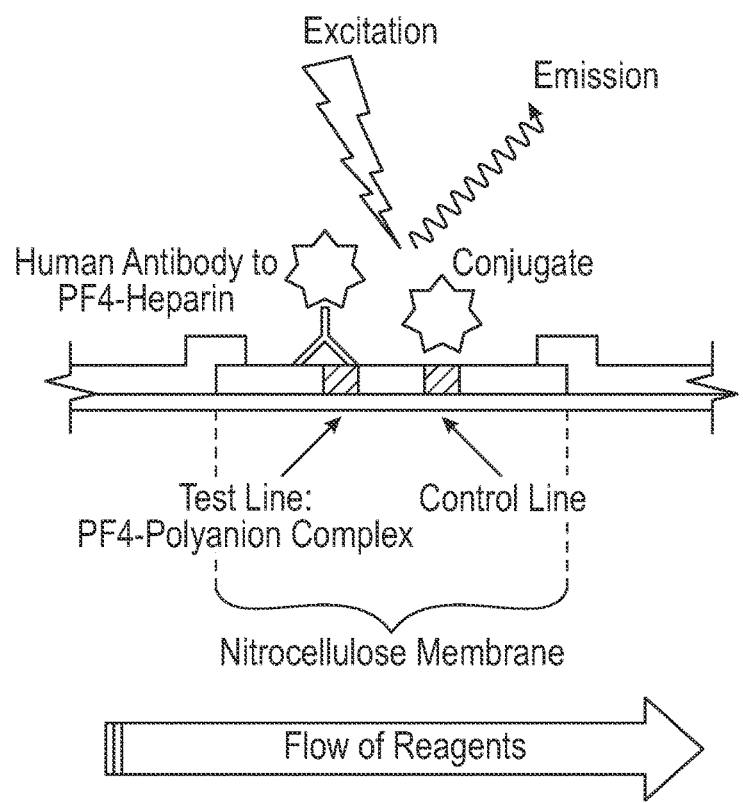
FIGS. 1A-1B depict the general layout of an assay device according to the present invention.
Figure 1B:
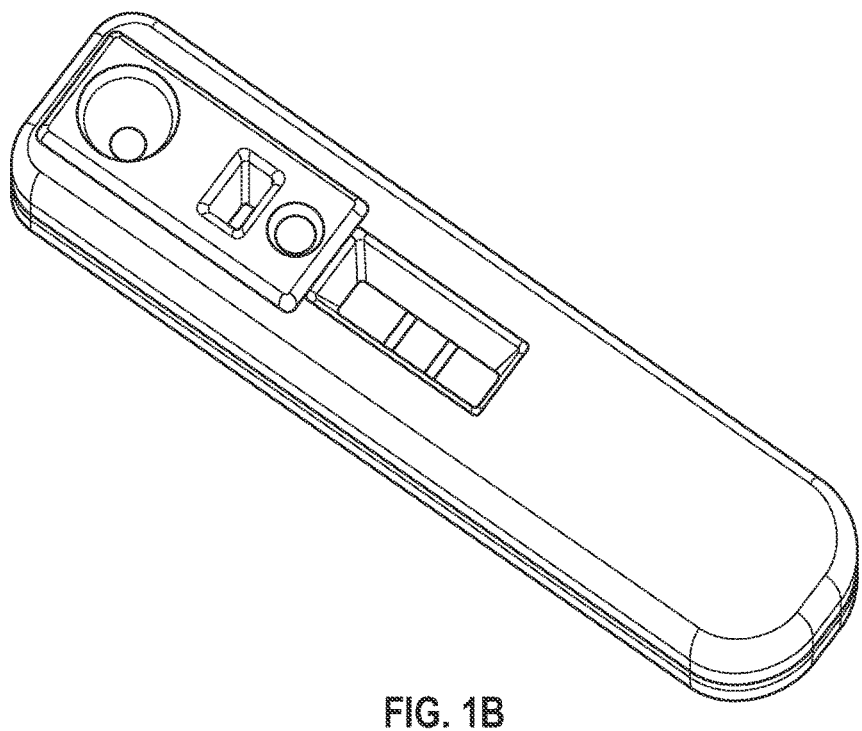

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

Approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value.

As used herein, the term "platelet factor 4" or "PF4" refers to a highly positively charged tetrameric protein with a molecular weight of approximately 32,000 Daltons found in the α-granules of platelets and released into the plasma following platelet activation. PF4, also known as CXCL4, further refers to a 70 amino acid protein substantially corresponding to the mature protein described by Poncz et al., Blood 1987, 69:219-23 and having any of the biological activities associated with PF4 such as immunostimulatory, chemotactic and heparin neutralization activities. The PF4 used in the present invention may be PF4 derived from human platelets, recombinant human PF4 or human PF4 manufactured by standard peptide synthesis.

The term "heparin" generally refers to any member of a family of structurally complex, sulfated glycosaminoglycans generally characterized by a structure of repeating glucosamine and glucuronic acid sugar residues (Casu, *Adv. Carbohyd. Chem. Biochem.* 1985, 47:578-83). The most widely known heparin is "unfractionated" or "commercial" heparin prepared from bovine lung or porcine gut, which encompasses a heterogeneous mixture of heparin molecules ranging from approximately 8,000 to 20,000 Daltons molecular weight (Wolinsky et al., *J. Am. Coll. Cardiol.* 1990, 15:475-81). However, the term "heparin" also encompasses a broad range of more homogeneous heparin preparations, as well as heparin-like molecules, including heparan sulfates and heparin having a hydrophobic counter-ion such as tridodecyl methylammonium and benzalkonium. Also included within the definition of heparin for the purposes of describing the invention are synthetic heparins and heparin derivatives, a variety of which have been produced using conventional chemical synthetic, modifying and degradative techniques (Roden, L. THE BIOCHEMISTRY OF GLYCOPROTEINS AND PROTEOGLYCANS (Lennarz, W. J., ed.) 267-371, Plenum Publishing Corp., New York, 1980, incorporated herein by reference). Variations include alkali metal or alkaline-earth metal salts of heparin, such as sodium heparin (e.g., hepsal or pularin), potassium heparin (e.g., clarin), lithium heparin, calcium heparin (e.g., calciparine), magnesium heparin (e.g., cutheparine), low molecular weight heparin (e.g., ardeparin sodium) with a molecular weight of from about 4,000 to about 5,000 Daltons and high affinity heparin (Scully et al., *Biochem. J.* 1989, 262:651-58).

As used herein, "PF4/heparin complex" refers to a complex formed when heparin binds to PF4 and induces a conformational change in the protein exposing a cryptic epitope. The complex is recognized as a "foreign" antigen and triggers an immune response, which is characterized by the release of immunoglobulins that bind to the PF4/heparin complex with subsequent clustering of the platelet Fc-receptors, resulting in platelet activation.

As used herein, the term "fluid" refers to any composition that can flow. Fluids thus encompass compositions that are in the form of semi-solids, pastes, solutions, aqueous mixtures, and other such compositions.

The term "sample" generally refers to anything which may contain the analyte for which an assay is desired, more specifically antibodies to the PF4/heparin complex. The sample may be a biological sample, such as a biological fluid or a biological tissue. Examples of biological fluids include blood, plasma, serum, saliva, serum, sputum, urine, cerebral spinal fluid, tears, mucus, amniotic fluid, semen, stool, or the like. Biological tissues are aggregate of cells, usually of a particular kind of together with their intercellular substance that form one of the structural materials of a human structure, including connective, epithelium, muscle and nerve tissues. Examples of biological tissues also include organs, tumors, lymph nodes, arteries and individual cells.

As used herein, "blood sample" refers to refers to a whole blood sample or a plasma or serum fraction derived therefrom. Preferably, the blood sample refers to a human blood sample such as whole blood or a plasma or serum fraction derived therefrom. The term "plasma" refers to the fluid, non-cellular component of the whole blood. Depending on the separation method used, plasma may be completely free of cellular components, or may contain various amounts of platelets and/or a small amount of other cellular components. Because plasma includes various clotting factors such as fibrinogen, the term "plasma" is distinguished from "serum," which refers to whole mammalian serum, such as whole human serum. Further, as used herein, "serum" refers to blood plasma from which clotting factors (e.g., fibrinogen) have been removed.

As used herein, the term "subject" or "patient" preferably refers to a human.

The term "polyanion" generally refers to a macromolecule having more than one negatively charged anionic group. As used herein, the term "anionic" refers to a linear, negatively charged, non-glycosaminoglycan (i.e. non-heparin) polymer having a molecular weight between 2000 and 6000 Daltons (median 5000 Daltons). As used herein, the polyanion is preferably selected from the group consisting of polyvinyl sulfonate, polystyrene sulfonate, polyanetholesulfonate, polyvinyl phosphate, polyvinyl phosphonate, polyvinyl sulfate, and a combination thereof. In particularly preferred embodiments, the polyanion is polyvinyl sulfonate (PVS).

As used herein, the term "PF4/polyanion complex" refers to a complex formed when a polyanion as defined herein binds to PF4 and induces a conformational change in the protein exposing a cryptic epitope. The PF4/polyanion complex is preferably selected from PF4/polyvinyl sulfonate, PF4/polystyrene sulfonate, PF4/polyanetholesulfonate, PF4/polyvinyl phosphate, PF4/polyvinyl phosphonate and PF4/polyvinyl sulfate. In particularly preferred embodiments, the PF4/polyanion complex is PF4/PVS.

As used herein, the term "polyvinyl sulfonate" or "PVS" refers to a molecule of the formula —[$CH_2$—CH—($SO_3Na$)—]$_n$— wherein n preferably ranges from 20 to 60, including salts of potassium and other cations. In the Examples below, the polyvinyl sulfonate had a molecular weight of about 5,000 Daltons (about 35-40 subunits).

The term "immobilized" generally means stationary or unable to move. As used herein, "immobilized" means that a molecule or molecular complex is at least partially, and preferably substantially, attached to a substrate at the molecular level (i.e., through a covalent or non-covalent bond or interaction). A skilled artisan will appreciate that the present invention is not limited by any particular immobilization mode.

The term "conjugate" generally refers to an antibody that is chemically bound to a fluorophore allowing visual detection of the antibody. As used herein, "conjugate" refers to an anti-human antibody (e.g., goat anti-human IgG, IgA, IgM, or a combination thereof) labeled with a non-particulate fluorescent dye. It is noted that other immunoglobulins (e.g., donkey, horse, sheep, rabbit, mouse, rat, llama, guinea pig, hamster and chicken) can also be used as anti-human antibodies and are contemplated for use in the present invention.

As used herein, the term "antibody" is used in the broadest sense. Therefore, an "antibody" may be naturally occurring or man-made such as monoclonal antibodies produced by conventional hybridoma technology and/or a functional fragment thereof. Antibodies of the present invention comprise monoclonal and polyclonal antibodies as well as fragments (such as Fab, Fab', F(ab')$_2$, Fv) containing the antigen binding domain and/or one or more complementarity determining regions of these antibodies.

The term "non-particulate" generally refers to a material that is not in a powder or a particulate form, that is, the material is not a powder, fragment, granule, grain or particle. As used herein, "non-particulate" refers to a liquid medium that preferably does not include a significant amount of discrete particles, meaning that at least 90%, more preferably at least 95%, and most preferably at least 99% of the material comprised in the medium is fully dissolved. As used herein, the term "fluorescent dye" or "fluorescent label" refers to a compound comprising at least one fluorophore that accepts radiant energy of one wavelength and emits radiant energy of a second wavelength.

The term "amine-reactive" generally refers to features or functional groups of a compound that will react with an amine group on a second compound. As used herein, the term "amine-reactive dye" refers to a water-soluble fluorescent dye selected from a DyLight™, an Alexa Fluor®, a HiLyte Fluor™, a CyDye™, a Cy®, a CF™, an IRDye®, and a combination thereof. In particularly preferred embodiments, the amine-reactive fluorescent dye is a DyLight™.

As used herein, the term "releasably attached" means that a labeled conjugate is dried on a test strip in a reversible fashion, i.e. the releasably attached conjugate is capable of moving along the test strip when resolubilized in the presence of a suitable running buffer.

The term "capture reagent" generally refers to a reagent capable of binding and capturing a target molecule in a sample such that under suitable condition, the capture reagent-target molecule complex can be separated from the rest of the sample. In a sandwich immunoassay, the capture reagent is preferably an immobilized antibody or a mixture of different antibodies against a target antigen. As used herein, the capture reagent is preferably immobilized in the control zone to capture unbound labeled conjugate. Accordingly, in the preferred embodiments, the capture reagent comprises an antibody that can bind the anti-human immunoglobulin used for detection. For example, if a goat anti-human IgG is used in the labeled conjugate, a mouse anti-goat antibody can be used as the capture reagent. It is noted that other immunoglobulins (e.g., donkey, horse, goat, sheep, rabbit, rat, llama, guinea pig, hamster and chicken, as long as they are not from the same species as the anti-human antibody) can also be used as capture reagents and are contemplated for use in the present invention.

As used herein, the term "lateral flow" refers to the placement of a bodily fluid sample suspected of containing human PF4/heparin antibodies on a test strip comprising absorbent or non-absorbent material, wherein the analyte in the fluid sample flows laterally through the test strip by capillary action, reacting with various reagents in the strip.

The term "test strip" generally refers to a chromatographic-like medium upon which an assay of the present invention is preferably performed. As used herein, the test strip contains in sequential order a "conjugate zone" positioned near the proximal end and comprising a non-particulate fluorescent label coupled to an anti-human antibody that binds to human immunoglobulins to form a detectable complex, a "sample zone" positioned downstream of the "conjugate zone" for the application of the fluid sample, a "detection zone" which contains an immobilized PF4/polyanion complex that captures and retains PF4/heparin antibodies in the fluid sample, a "control zone" which contains an immobilized capture reagent that captures and retains the labeled conjugate, and a "wicking pad" positioned at or adjacent the distal end to help draw the fluid sample through the test strip.

As used herein, the terms "upstream" and "proximal" generally refer to the direction of fluid flow away from the end of the detection system and toward the site of sample application. Conversely, the terms "downstream" and "distal," as used herein, generally refer to the direction of fluid flow away from the site of sample application and toward the end of the detection system.

The term "in fluid communication" as used herein in reference to structures means that the structures are connected so that a fluid flowing in one structure flows directly or indirectly to the other structure. The term "in fluid communication" as used herein with reference to an element of the device refers to a state in which the device, after being wetted by a fluid sample, may permit the flow or diffusion of fluid sample or components of the fluid sample through or into one or more portions of that element. The term further refers to a condition in which two or more particular elements are wetted by the fluid sample.

The term "conjugate pad" generally refers to a membrane or other type of material that can comprise a labeled conjugate. As used herein, "conjugate pad" can further comprise a sample zone positioned downstream of the conjugate zone. The conjugate pad can be made of cellulose acetate, cellulose nitrate, polyamide, glass fiber, membrane, polyethersulfone, regenerated cellulose (RC), polytetra-fluorethylene (PTFE), polyester (e.g. polyethylene terephthalate), polycarbonate (e.g., 4,4-hydroxy-diphenyl-2,2'-propane), aluminum oxide, mixed cellulose ester (e.g., mixture of cellulose acetate and cellulose nitrate), nylon (e.g., polyamide, hexamethylene-diamine, and Nylon 66), polypropylene, polyvinylidene fluoride (PVDF), high-density polyethylene (HDPE), and HDPE+nucleating agent "aluminum dibenzoate" (DBS). Other examples of conjugate pads include Cyclopore® polyethylene terephthalate, Nucleopore® polyethylene terephthalate, Membra-Fil® cellulose acetate and nitrate, Whatman® cellulose acetate and nitrate, Whatman® #12-S rayon, Anopore® aluminum oxide, Anodisc® aluminum oxide, Sartorius cellulose acetate, e.g. 5 µm, and Whatman® Standard 17 bound glass.

The term "sample pad" generally refers to a hydrophilic element, such as a hydrophilic membrane, that can be used to receive a sample, such as a sample of blood, serum, or plasma. As used herein, the sample pad can be either a part of the conjugate pad or a discrete pad positioned downstream of, and in fluid communication with, the conjugate pad. The sample pad is preferably made of the same material as the conjugate pad.

As used herein, the term "porous membrane" generally refers to a membrane having a multiplicity of pores or holes that is capable of transporting a liquid by capillary forces over a distance. The membrane is preferably capable of binding reactants in the detection zone, and optionally, in other regions of interest, either by covalent attachment, non-covalent attachment, or physical attachment. Suitable porous membrane materials for use in the present invention include natural or synthetic fiber, such as nylon, polyester, cellulose-based polymeric substances, sintered structures composed of particulate materials such as glass or various thermoplastic polymers; or cast membrane films, often synthetic, such as nitrocellulose, nylon, polysulfone and the like. The preferred thickness and the medium pore size of the porous membrane depend, in part, on the nature of the sample which is to be applied to the membrane, and the desired rate of fluid flow through the porous media, the test time and the test sensitivity. Determination of the most preferred pore size for any particular application is within the knowledge of those skilled in the art. As a general matter, a pore size of between 3 µm and 12 µm is preferred. In particularly preferred embodiments of the present invention, the porous membrane is made of nitrocellulose.

As used herein, the term "wet pad" refers to an optional test strip element that is positioned on the upstream end of the assay device and in fluid communication with the conjugate pad. When used, the "wet pad" serves to receive a conjugate buffer which solubilizes the dried conjugate and drives it toward the detection zone. The wet pad is preferably made of the same material as the conjugate pad. Despite its name, the term "wet pad" does not in any way imply that this structural element is inherently wet at all times.

As used herein, the term "wicking pad" refers to a test strip element that is in fluid communication with the opposite end of the porous membrane from the sample zone on the downstream end of the assay device. The wicking pad enhances capillary flow in the porous membrane by "pulling," or "driving" the fluid through the porous membrane. The wicking pad for use in the present invention may be made of any material that is capable of rapidly absorbing liquid from the test strip. The absorbent material used for any given test is of sufficient volume to absorb at least as much liquid drawn from the test strip by capillary forces in order that the analyte and other material from the conjugate/sample pad crosses the detection and control zones. Suitable materials include any one of a number of known paper or cellulose based materials such as pure cellulose, nitrocellulose or filter paper.

As used herein, "contacting" means bringing two or more components together. "Contacting" can be achieved by mixing all the components in a fluid or semi-fluid mixture. "Contacting" can also be achieved when one or more components are brought into physical contact with one or more other components on a solid surface such as a solid tissue section or a substrate.

As used herein, the term "assessing" or "measuring" is intended to include both quantitative and qualitative determination in the sense of obtaining an absolute value for the amount or concentration of the analyte present in the reaction system, and also of obtaining an index, ratio, percentage, visual or other value indicative of the level of analyte in the reaction system.

As used herein, the term "point of care" refers to a medical diagnostic procedure that is particularly adapted for use in the immediate vicinity of the patient being treated.

B. Assay Devices for Detecting PF4/Heparin Antibodies

The lateral flow assay described herein is a qualitative and semi-quantitative, point-of-care immunoassay for heparin-induced antibodies that can be used to screen for antibodies associated with heparin-induced thrombocytopenia, referred to as PF4/heparin antibodies. The in vivo antibodies are formed against a complex of PF4 and heparin, however in vitro these antibodies react with PF4 when it is complexed to other polyanions such as polyvinyl sulfonate (PVS). Detailed description of the cross-reactivity of PF4/heparin antibodies with various PF4/polyanion complexes is provided in U.S. Pat. No. 5,972,718, the content of which is incorporated herein by reference in its entirety.

It is a rapid immunochromatographic sandwich assay using human PF4 complexed with a polyanion and anti-human IgG, or a mixture of anti-human IgA, IgG and IgM, antibodies conjugated with a non-particulate fluorescent label, preferably an amine-reactive fluorescent dye. The PF4/polyanion complex is immobilized in a test line (detection zone) of an assay device, and the non-particulate fluorescent dye labeled anti-human antibodies (conjugate) are releasably attached to a conjugate pad upstream of the test line. As noted above, the labeled antibodies are also positioned upstream of the sample application site (sample zone) to prevent the interaction of the human antibodies and conjugate prior to their interactions at the test line. The test is analyzed using an electro-optical reader device that has the ability to measure the degree of interaction of the analyte, human antibodies to the PF4/heparin complex, based upon the fluorescent signal, e.g., a fluorometer. Test performance is assessed by a reference line (control zone) that contains an immobilized capture reagent that binds the anti-human antibodies comprised in the conjugate, e.g., mouse anti-goat IgG if the conjugate includes goat anti-human antibodies.

Figure 2A:
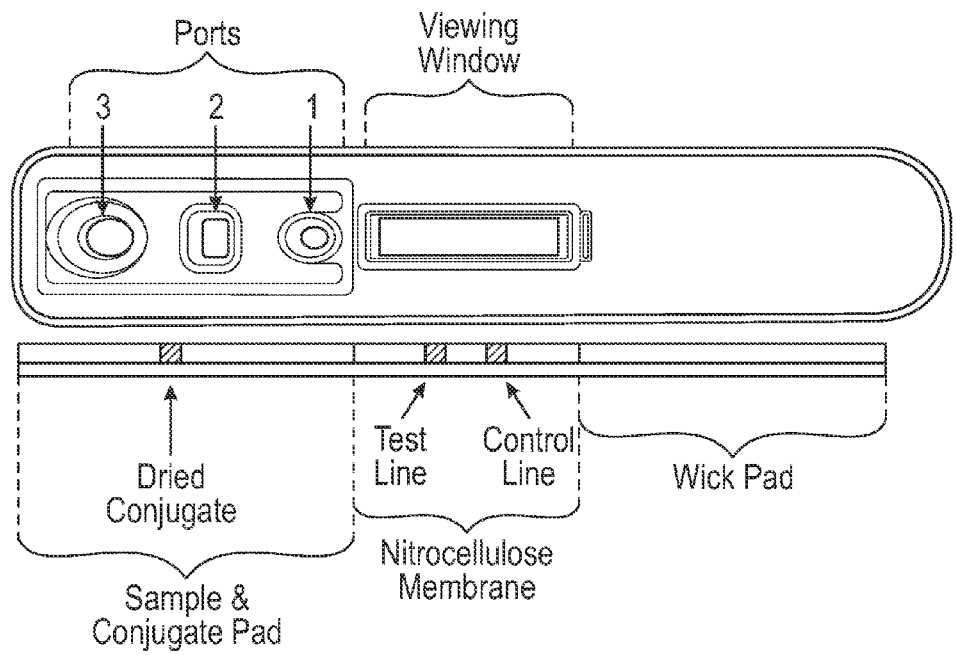
FIGS. 2A-2C further illustrate the general layout of an assay device according to the present invention.
Figure 2B:
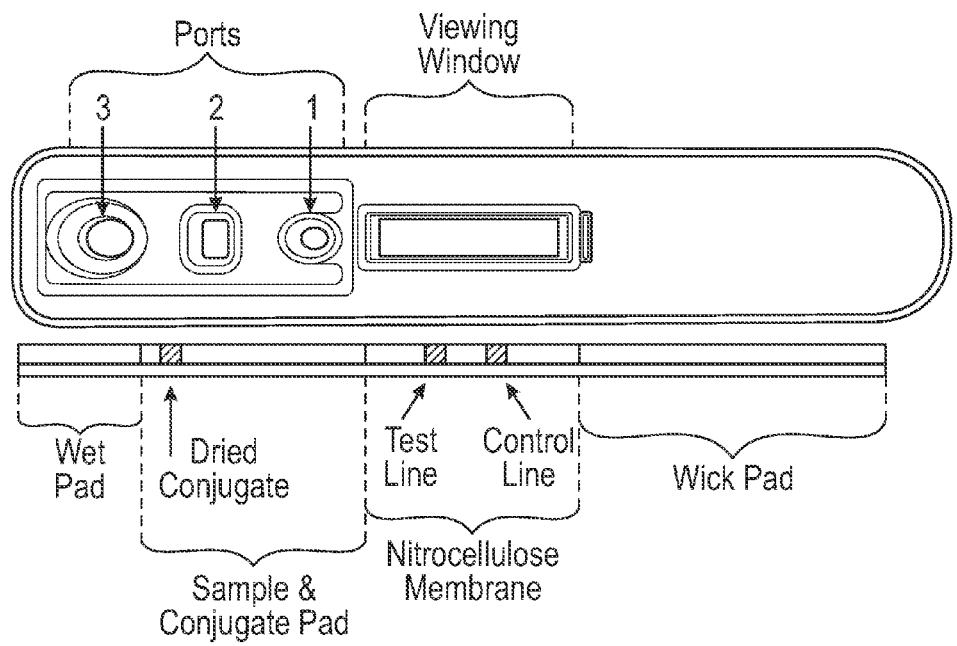
Figure 2C:
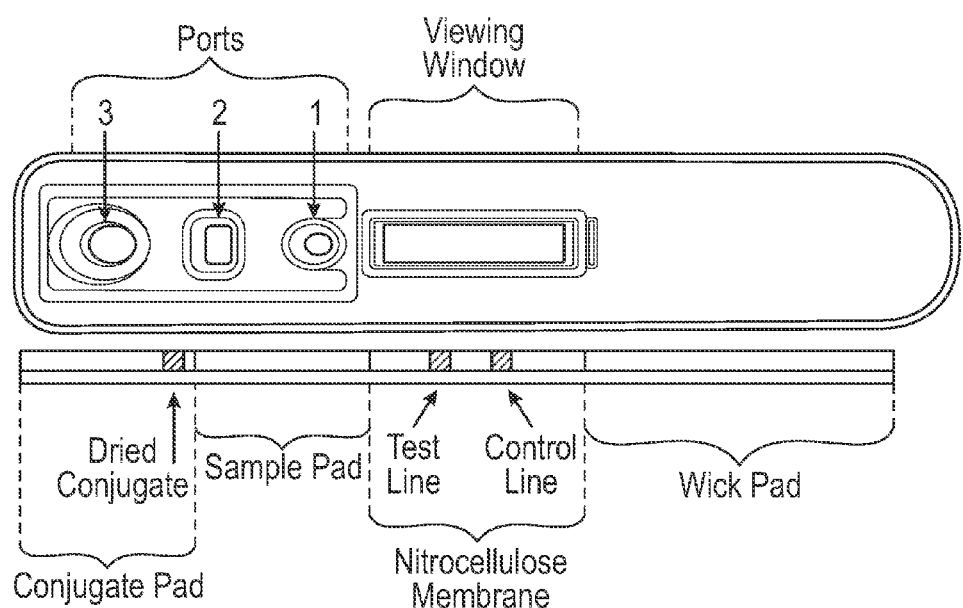

In preferred embodiments, the present lateral flow PF4/heparin assay contains a test strip enclosed in a cassette. FIGS. 2A-2C illustrate the various components and structure of some exemplary embodiments of the test device. At each membrane and/or pad juncture, there is an overlap of the membrane and/or pad materials so that the pads and/or membrane are in fluid communication with each other. In some embodiments, illustrated in FIG. 2C, the test strip has four components, from upstream to downstream: (1) a conjugate pad containing a conjugate zone; (2) a sample pad containing a sample zone; (3) a porous membrane containing a detection zone and a control zone; and (4) a wicking pad. In preferred embodiments, illustrated in FIGS. 2A-2B, the conjugate and sample pads are combined into a single, integral pad provided that the conjugate is dried on the most distal portion of the pad and the sample is applied to its most proximal portion. The test strip further preferably includes a sample buffer zone, positioned between the sample and conjugate zones, and a conjugate buffer zone, positioned upstream of the conjugate zone. In some embodiments, illustrated in FIG. 2B, the test strip further contains a discrete wet pad upstream of the conjugate pad. In these embodiments, the conjugate buffer zone is positioned within the wet pad instead of the conjugate pad.

The conjugate pad is preferably made of polyester and contains releasably attached, non-particulate fluorescent dye labeled anti-human IgG, or a mixture of anti-human IgG, IgM and IgA, antibodies that will bind to the analyte human antibodies to the PF4/heparin complex. In preferred embodiments, the labeled antibodies are goat anti-human IgG. The non-particulate fluorescent label preferably comprises an amine-reactive dye, such as a DyLight™, an Alexa Fluor®, a HiLyte Fluor™, a CyDye™, a Cy®, a CF™, an IRDye®, or a combination thereof. The amine-reactive fluorescent dye label is soluble in an aqueous solution and is not a particle or particulate label. (See, e.g., Thermo Fisher Scientific Inc., Instructions for DyLight™ Microscale Antibody Labeling Kits, stating that "the water solubility of the DyLight Reagents allows a high fluor-to-protein ratio without precipitation during conjugation.") The amine-reactive fluorescent dye label is preferably directly conjugated to anti-human antibodies, such as goat anti-human IgG, or a mixture of goat anti-human IgG, IgM and IgA.

The porous membrane is preferably made of nitrocellulose. The detection zone preferably contains an immobilized PF4/polyanion complex to which the analyte human PF4/heparin antibodies bind. The control zone preferably contains an immobilized capture reagent that binds to the unbound labeled antibodies that travel past the detection zone. The immobilized capture reagent is preferably an antibody that binds to immunoglobulins from the mammalian species used to generate the anti-human antibodies for the conjugate. For example, if the anti-human antibodies are raised in goat, the capture reagent may comprise an anti-goat antibody, such as a mouse anti-goat IgG.

Referring again to FIGS. 2A-2C, the test strip is enclosed in a cassette. Port 1 is configured to expose the sample zone and used to apply a sample, preferably serum or plasma, to the conjugate pad (or the sample pad, if a discrete sample pad is used). Ports 2 is configured to expose the sample buffer zone and used to apply a sample buffer to the conjugate pad (or the sample pad, if a discrete sample pad is used). Finally, port 3 is configured to expose the conjugate buffer zone and used to apply a conjugate buffer to the conjugate pad (or the wet pad, if a discrete wet pad is used). In some embodiments, each of ports 2 and 3 is covered by a pouch that contains a sample buffer and a conjugate buffer, respectively, which may have the same or different compositions. In preferred embodiments, the sample and conjugate buffers have the same composition, containing 1×PBS, 1% BSA, and 0.1% polysorbate 20 (Tween 20™), and buffered to pH 7.4.

In some embodiments, the right hand side of the cassette preferably houses a radio frequency identification (RFID) chip, which contains the assay parameters as well as lot information (product name, lot number, expiration date). The right hand side of the cassette is inserted into the electro-optical reader, e.g., a fluorometer, for reading the assay signal.

Figure 3A:
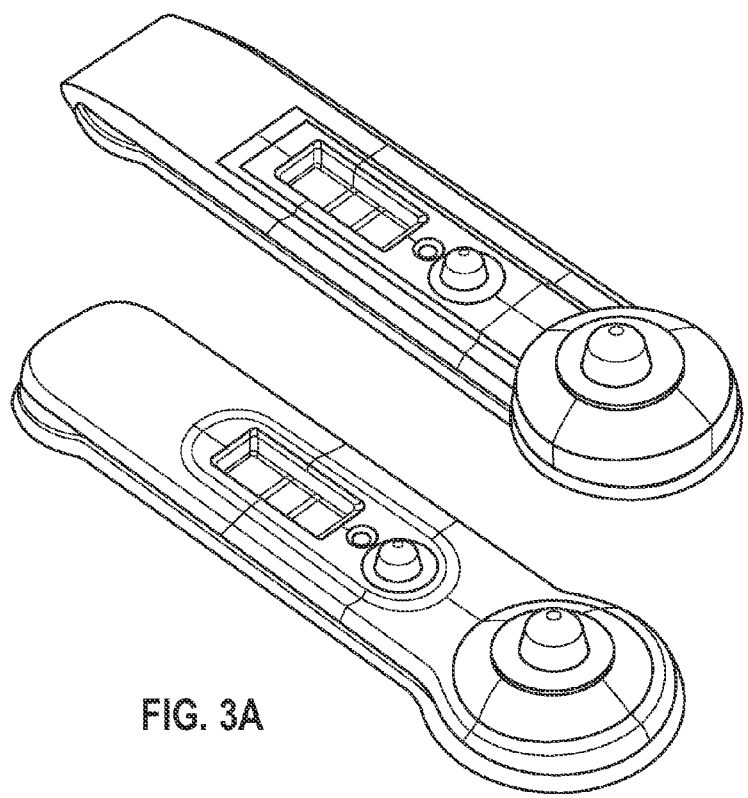
FIGS. 3A-3B illustrate an alternative embodiment of the assay device according to the present invention.
Figure 3B:
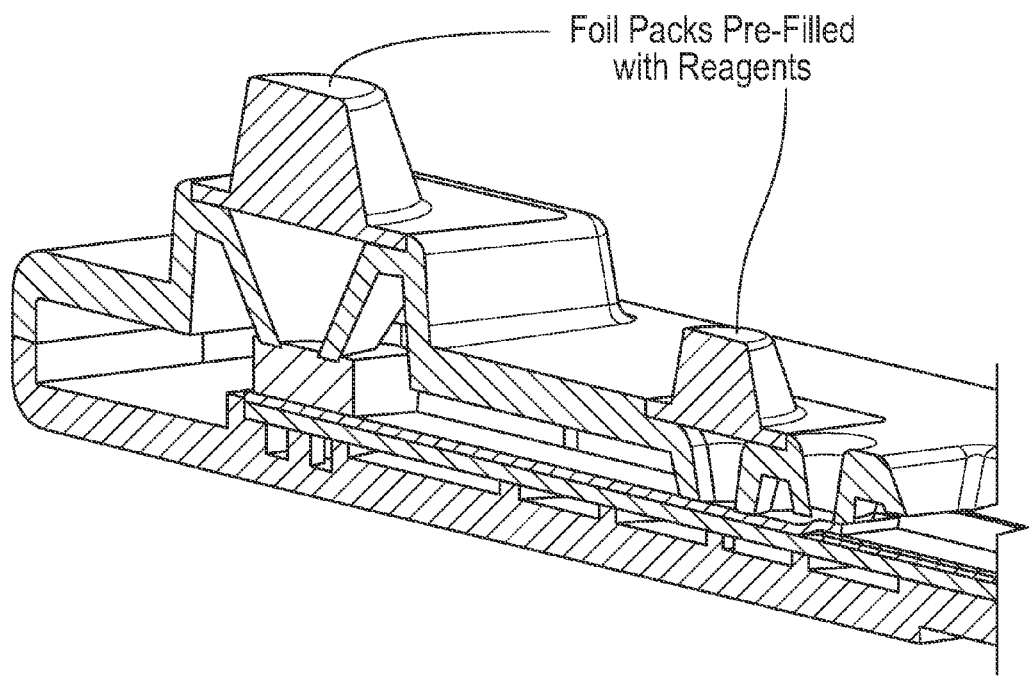
Figure 4A:
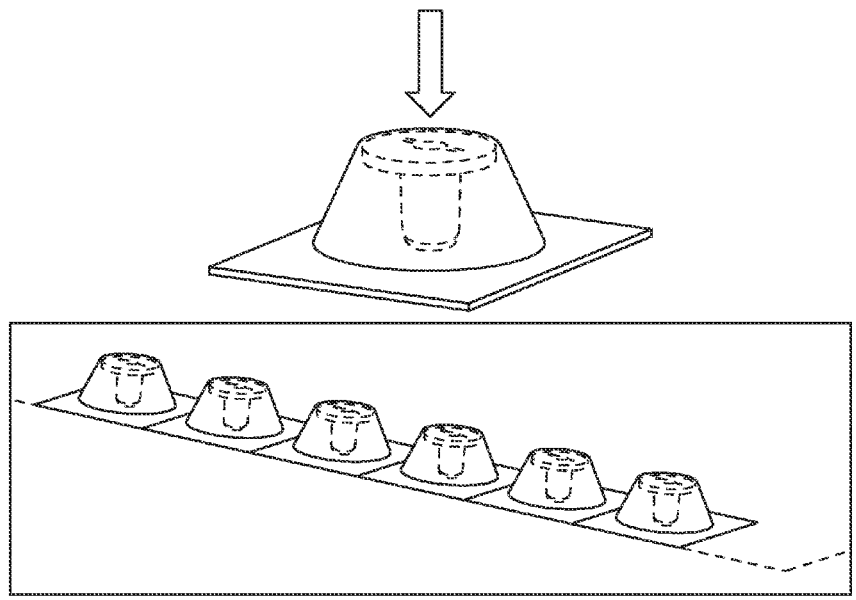
FIGS. 4A-4B show examples of the piercing mechanisms that can be used in the device embodiment shown in FIGS. 3A-3B to break the blisters/pouches and deliver the sample and conjugate buffers contained therein to the test strip.
Figure 4B:
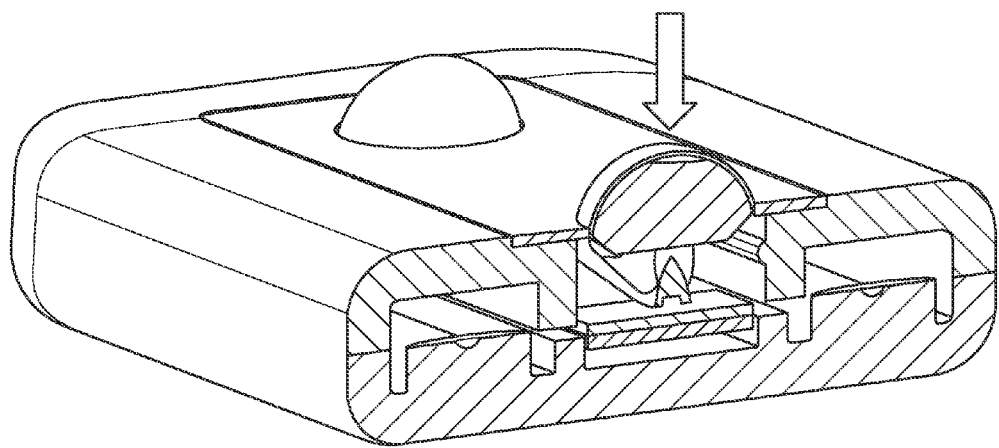

In one alternative embodiment, an assay device as illustrated in FIGS. 3A-3B may be used. In these embodiments, pouches positioned directly over ports 2 and 3 are pre-filled with the sample and conjugate buffers, respectively. The pouches are preferably covered by blisters made of a flexible material, e.g., rubber, latex, plastic etc., such that the pouches can be broken when the operator applies a positive pressure to the blisters. FIGS. 4A-4B provide illustrative examples of piercing mechanisms that can be used to break the pouches to release the buffers contained therein. It will be appreciated that these examples are non-limiting and alternative means for releasing the buffers may also be used.

Figure 5A:
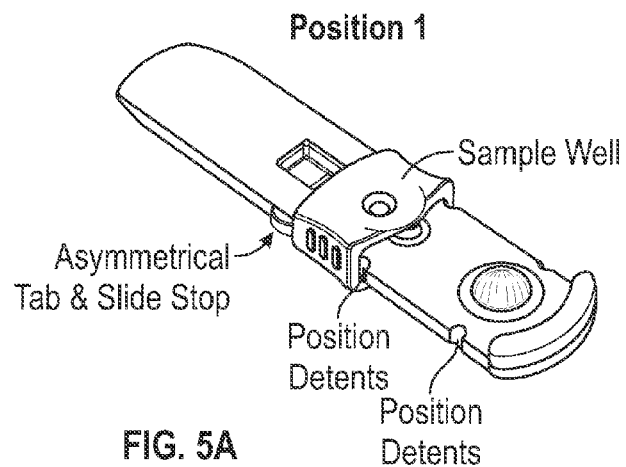
FIGS. 5A-5C illustrate a modification of the device shown in FIGS. 3A-3B, which includes an indicator slide slidably positioned around the assay cassette and having a leading edge shaped to compress the blisters/pouches containing the sample and conjugate buffers as the slide moves relative to the cassette.
Figure 5B:
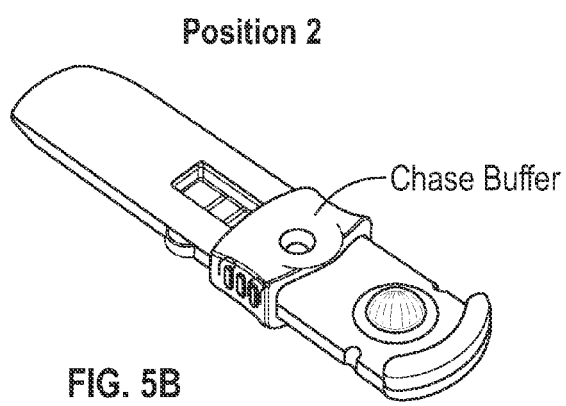
Figure 5C:
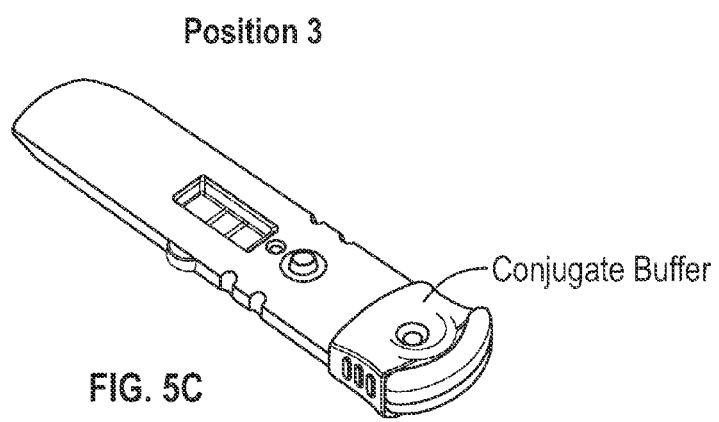

In another alternative embodiment, an assay device as illustrated in FIGS. 5A-5C may be used. While this embodiment is conceptually similar to the embodiment shown in FIGS. 3A-3B, it has one significant modification. The device of this embodiment includes an indicator slide having a leading edge that is shaped to compress the blisters and/or pouches that contain the buffers. Accordingly, release of the buffers can be easily and conveniently accomplished by a lateral movement of the indicator slide relative to the assay cassette.

C. Methods for Detecting PF4/Heparin Antibodies

In operation, the PF4/heparin antibody assay described herein is conducted in three basic steps: (1) sample addition, (2) addition of a sample buffer, and (3) flow of the conjugate. In one embodiment, the sample is first added to port 1 to contact with the sample zone of the conjugate pad or sample pad. Next, a sample buffer, which preferably contains 1×PBS, 1% BSA, and 0.1% Tween 20™, and is buffered to pH 7.4, is immediately applied to port 2 to "push" the sample to the detection zone, where the PF4/heparin antibodies, if present in the sample, bind to the immobilized PF4/polyanion complex. After a dwell time, which can be as short as one second but preferably is at least about three minutes after the sample buffer is added, a conjugate buffer is applied to port 3. The conjugate buffer, which is preferably the same as the sample buffer, hydrates and solubilizes the dried conjugate, allowing the labeled anti-human antibodies to flow to the detection and control zones, where they bind with the immobilized PF4/heparin antibodies bound to the PF4/polyanion complex and to the capture reagent, respectively.

In the alternative assay embodiment illustrated in FIGS. 3A-3B, the sample is first added to port 1. The pouch over port 2 is then broken immediately after addition of the sample, releasing the sample buffer. The sample buffer pushes the sample to the detection zone, where the PF4/heparin antibodies, if present in the sample, bind to the immobilized PF4/polyanion complex. The pouch over port 3 is broken after a dwell time, which can be as short as one second but preferably is at least about three minutes, after the pouch over port 2 has been broken. The conjugate buffer dispensed at port 3, which is preferably the same as the sample buffer, hydrates and solubilizes the dried conjugate, allowing the labeled anti-human antibodies to flow to the detection and control zones, where they bind with the immobilized PF4/heparin antibodies bound to the PF4/polyanion complex and to the capture reagent, respectively.

In the alternative assay embodiment illustrated in FIGS. 5A-5C, the indicator slide is initially positioned over sample well, which corresponds to port 1 in FIGS. 2A-2C (see FIG. 5A). Detents in cassette are used to indicate proper alignment. The sample is first added to the sample well. After the sample addition, the indicator slide is moved to the second position to release the sample buffer from the first (small) blister (see FIG. 5B). The sample buffer pushes the sample to the detection zone, where the PF4/heparin antibodies, if present in the sample, bind to the immobilized PF4/polyanion complex. After a dwell time, which can be as short as one second but preferably is at least about three minutes after the buffer release from the first blister, the indicator slide is moved to the third position to release the conjugate buffer from the second (large) blister (see FIG. 5C). The conjugate buffer released from the second blister, which is preferably the same as the sample buffer, hydrates the dried conjugate, allowing the labeled anti-human antibodies to flow to the detection and control zones, where they bind with the immobilized PF4/heparin antibodies bound to the PF4/polyanion complex and to the capture reagent, respectively.

As noted above, if the test sample contains a detectable level of human antibodies to PF4/heparin, the detection zone will contain a labeled anti-human antibodies-PF4/heparin antibodies-PF4/polyanion sandwich complex. If the assay is properly run, the control zone will contain a labeled anti-human antibodies-capture reagent complex regardless of whether the test sample contains a detectable level of human PF4/heparin antibodies or not. After the sample is applied to the lateral flow PF4/heparin assay device described herein for preferably about 15 minutes, the fluorescent signals in the detection zone and the control zone are quantified by an electro-optical reader instrument, such as a fluorometer, to determine the presence and relative potency of human PF4/heparin antibodies in the test sample. The value measured at the control line and serves as a conjugate and flow distance control, but may further be used in the determination of the result at the test line. In some embodiments, standards may be provided to the user and a standard curve may be generated as part of the test to quantify, i.e. precisely determine or measure the amount of, human PF4/heparin antibodies in the sample.

D. Assay Systems for Detecting PF4/Heparin Antibodies

As noted above, the present invention also provides a point-of-care lateral flow immunoassay system for determining the presence and/or quantity of PF4/heparin complex induced immunoglobulin antibodies in a body fluid of a patient. The system includes a linear membrane of an inert, fibrous material capable of supporting a movement of liquids by capillary action and which in turn, is supported by a backing; a means for binding a light absorbing label to PF4/heparin complex induced immunoglobulin antibodies present in a sample of the body fluid passing through the conjugate zone; and a means for immobilizing on the membrane in the detection zone, a PF4/polyanion complex. The linear membrane is zoned, from proximal end to distal end, into a conjugate zone, a sample pad, a detection zone, a control zone, and a wicking pad, each optionally separated from its adjacent zone by a flow zone. The PF4/polyanion complex is capable of conjugatively binding to PF4/heparin complex induced immunoglobulin antibodies bound to the light absorbing label passing into the detection zone, wherein the light absorbing label facilitates the visibility of antibodies bound to the PF4/polyanion complex immobilized in the detection zone.

As noted above, the body fluid may be blood or an immunoglobulin-containing component thereof, such as plasma or serum. The polyanion is preferably selected from the group consisting of polyvinyl sulfonate, polystyrene sulfonate, polyanetholesulfonate, polyvinyl phosphate, polyvinyl phosphonate, polyvinyl sulfate, and a combination thereof. In particularly preferred embodiments, the polyanion is polyvinyl sulfonate (PVS). In some embodiments, the PF4/heparin complex induced immunoglobulin antibodies are selected from the group consisting of IgG, IgA, IgE, IgM, and a combination thereof. In certain preferred embodiments, the light absorbing label is a fluorescent label, and the visibility of the antibodies is facilitated by an electro-optical reading device, such as a fluorometer.

EXAMPLES

Example 1

Preparation of PF4/Heparin Lateral Flow Assay Device

A polyester conjugate pad was blocked with a blocking buffer containing 10 mM borate, 3% bovine serum albumin (BSA), 1% polyvinylpyrrolidone (MW 40,000, PVP-40), 0.25% Triton X-100 (octylphenol ethylene oxide), and 0.05% 2-methyl-4-isothiazolin-3-one and 5-chloro-2-methyl-4-isothiazolin-3-one (ProClin®), pH 8.0. An amine-reactive fluorescent dye label (DyLight™ N-hydroxysuccinimide (NHS) ester, Thermo Fisher Scientific Inc., Rockford, Ill.), was directly conjugated to a mixture of goat anti-human IgA, IgG and IgM antibodies according to the manufacturer's instructions (Instructions for DyLight™ Microscale Antibody Labeling Kits, Thermo Fisher Scientific Inc., Rockford, Ill.). The amine-reactive fluorescent dye labeled goat anti-human IgG antibody conjugate was dissolved in a buffer containing phosphate buffered saline (PBS), 0.05% ProClin®, 7% sucrose, and 3% trehalose, applied and dried on the conjugate pad.

A nitrocellulose membrane was blocked with a blocking buffer containing 10 mM sodium phosphate, 1% sucrose, 0.25% PVP-40, and 0.8% fish gel, pH 7.6. A PF4/PVS complex was prepared as described previously in U.S. Pat. No. 5,972,718, dissolved in a buffer containing 2.8 mM $KH_2PO_4$, 7.2 mM $Na_2HPO_4$, 128.3 mM NaCl, and 0.1% $NaN_3$, applied and dried in the detection zone of the nitrocellulose membrane. A mouse anti-goat IgG antibody was dissolved in a buffer containing PBS and 0.05% $NaN_3$, applied and dried in the control zone of the nitrocellulose membrane. Other than the blocking steps, the conjugate pad and nitrocellulose membrane were not subjected to any other chemical treatments.

The conjugate pad, the nitrocellulose membrane and a cellulose-based wicking pad were assembled on a solid backing so that both pads overlap with the membrane, and the entire assembly was enclosed in a plastic cassette along with a radio frequency identification (RFID) chip.

Example 2

PF4/Heparin Lateral Flow Assay Protocol

The lateral flow assay protocol was as follows. A 5 µl serum sample was applied to the sample port, shown as port 1 in FIGS. 1A-1C, and 15 µl of sample buffer (1×PBS, 1% BSA, and 0.1% polysorbate 20 (Tween 20™), pH 7.4) was immediately applied to the sample buffer zone, shown as port 2 in FIGS. 2A-2C. After approximately 3 minutes, 90 µl of conjugate buffer (1×PBS, 1% BSA, and 0.1% polysorbate 20 (Tween 20™), pH 7.4) was applied to the conjugate buffer zone, shown as port 3 in FIGS. 2A-2C. After approximately 12 minutes, the assay cassette was placed into a fluorescence reader, and fluorescent signals from the amine-reactive fluorescent label were measured at the detection and control zones. Each sample was tested in the PF4/heparin lateral flow assay using replicates of 4.

Example 3

Comparative Performance of PF4/Heparin Lateral Flow Assay

To compare the relative performance of PF4/heparin lateral flow assay with that of a reference PF4/heparin enzyme immunoassay, a sample set of 83 sera from patients on heparin therapy was tested in a PF4/heparin lateral flow assay according to the present invention and a commonly used ELISA test, which is described in detail in U.S. Pat. No. 5,972,718. In the ELISA, a PF4/PVS complex immobilized in microwells reacts with PF4/heparin antibodies from a patient sample with subsequent detection via an alkaline phosphatase conjugate (PF4 Enhanced®, Gen-Probe GTI Diagnostics, Inc., Waukesha, Wis.). Both assays detect IgG, IgA, and IgM antibodies. The PF4/heparin lateral flow assay was carried out as described in Examples 1 and 2 above, with the exception that the labeled anti-human antibody conjugate was applied to the conjugate pad in liquid form shortly after the sample buffer was applied to the sample buffer zone. Because the labeled conjugate was already solubilized when applied to the conjugate pad, no conjugate buffer was used to push the conjugate. In addition, no plastic housing/cassette was employed in this experiment.

The qualitative results were analyzed using a 2×2 contingency table. Positive and negative results for the PF4/heparin lateral flow assay were determined by assigning a preliminary cutoff based on the clinically negative sample showing the highest relative fluorescence unit (RFU) values. The results are summarized in Table 1 below. There were no false negatives in the lateral flow assay. Three samples showed positive reactivity in the lateral flow assay but were negative in the comparative ELISA assay. These samples were known positive samples diluted to a point slightly below the ELISA sensitivity cutoff. Overall, the PF4/heparin lateral flow assay showed 100% sensitivity (95% Confidence Interval (CI)=90.4%-100.0%), 93.6% specificity (95% CI=82.8%-97.8%), and 96.4% agreement with the reference enzyme immunoassay (95% CI=89.9%-98.8%).

TABLE 1

Relative performance of PF4/heparin lateral flow assay compared to ELISA

| | | PF4 Enhanced ® ELISA | | |
| --- | --- | --- | --- | --- |
| | | Positive | Negative | Total |
| PF4/Heparin Lateral Flow Assay | Positive | 36 | 3 | 39 |
| | Negative | 0 | 44 | 44 |
| | Total | 36 | 47 | 83 |

Example 4

Interference Testing of PF4/Heparin Lateral Flow Assay

Bilirubin, hemoglobin and triglycerides are commonly present in blood samples and can interfere with assay performance. Testing for interference by these substances was performed by "spiking" experiments. Triglyceride interference was assessed using intralipid (20% fat emulsion). The tested serum samples demonstrated negative, low positive and moderately positive PF4/heparin reactivity levels, as determined by ELISA. Sera prepared using an equivalent volume of the diluents for the corresponding substance tested (water for hemoglobin and triglycerides; 0.1N sodium hydroxide for bilirubin) were used as controls. All the samples were tested in triplicate. Table 2 below summarizes the interferents tested.

TABLE 2

Summary of interfering substances tested in PF4/heparin lateral flow assay

| Substance | Concentration Tested (mg/dL) |
| --- | --- |
| Bilirubin | 20 |
| Hemoglobin | 500 |
| Triglycerides (intralipid) | 500 |

Figure 6:
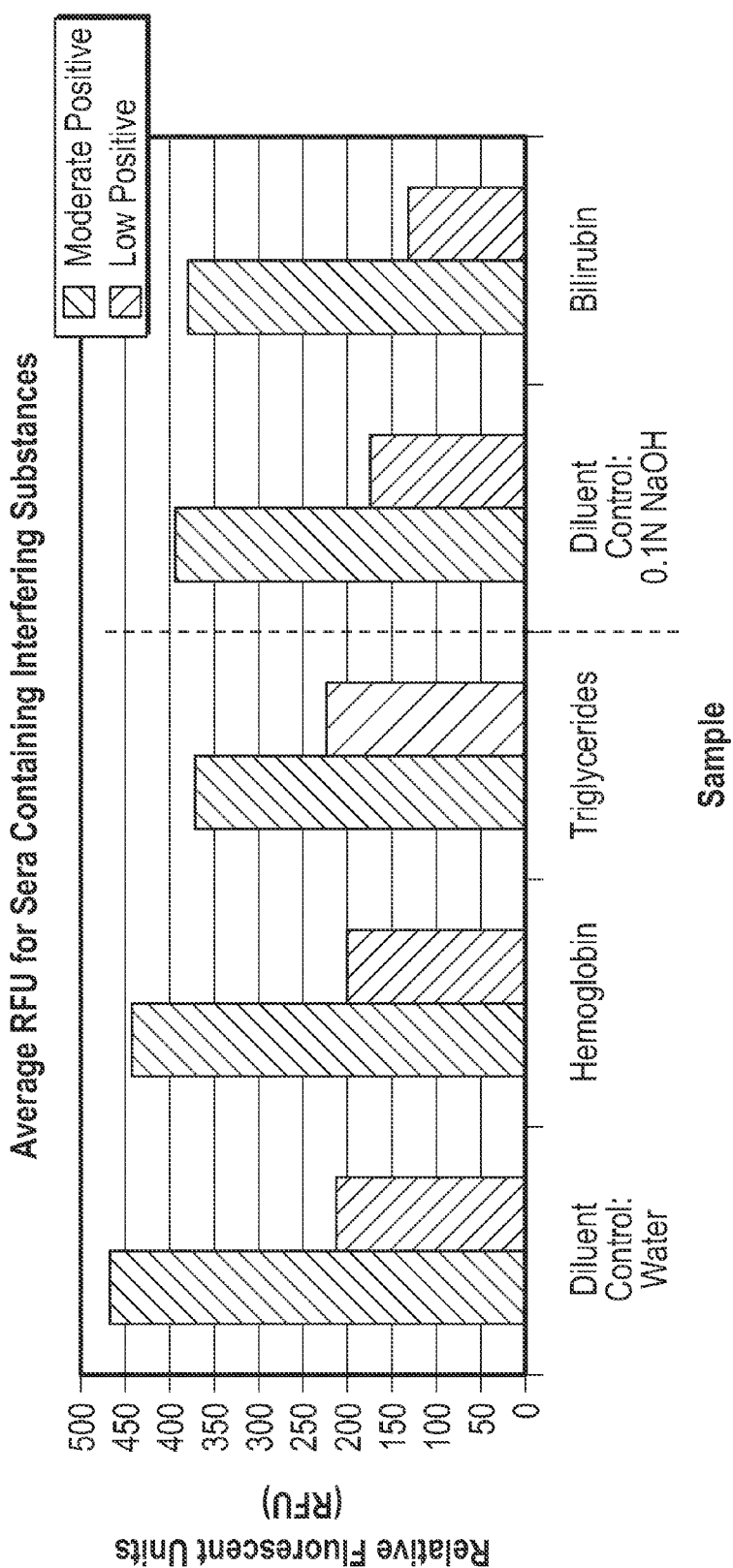
FIG. 6 illustrates the effects of hemoglobin, bilirubin and triglycerides on the performance of a PF4/heparin lateral flow assay according to the present invention.

Results of this experiment are summarized in FIG. 6. For each sample tested with each of the three substances, the calculated result remained approximately the same as compared to the diluent control. FIG. 6 shows that the average RFU values for test sera did not markedly differ from the corresponding control conditions. At the concentrations tested, bilirubin, hemoglobin and triglycerides did not appear to cause a significant interference with the PF4/heparin lateral flow assay.

Example 5

Cross-Reactivity Testing of PF4/Heparin Lateral Flow Assay

Cross-reactivity testing was performed in triplicate according to the assay protocol described in Example 2. Sera containing antibodies to the indicated antigens were tested in the absence of PF4/heparin antibodies. No cross reactivity was observed in the assay for antibodies to human platelet antigens (HPA), platelet glycoprotein IV (GPIV or CD36), phospholipids or blood group antigens (A, B or AB).

Based on the foregoing, the lateral flow assay described herein can be used for the detection of antibodies specific for the PF4/heparin complex. It may be used in screening for the presence of PF4/heparin antibodies which are implicated in heparin-induced thrombocytopenia (HIT). This assay format lends itself to point-of-care testing of individual samples. Readily available immunoassays for rapid detection (approximately 15 minutes) of antibodies against the PF4/heparin complex will allow for rapid confirmation of the clinical diagnosis of HIT and therefore may assist in the time-sensitive clinical management of HIT.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The invention claimed is:
1. A device for detecting the presence of human platelet factor 4 (PF4)/heparin antibodies in a fluid sample, the device comprising:
a PF4/polyanion complex immobilized on a solid support and an anti-human antibody labeled with a non-particulate fluorescent dye in a lateral flow format, the labeled anti-human antibody being releasably attached to the solid support upstream of:
the immobilized PF4/polyanion complex; and
a fluid sample zone configured to receive the fluid sample;
wherein the solid support is a test strip comprising:
a conjugate pad comprising:
(i) a conjugate zone containing the labeled anti-human antibody;
(ii) the fluid sample zone, the fluid sample zone being positioned downstream of the conjugate zone; and

(iii) a sample buffer zone configured to receive a sample buffer that facilitates lateral transport of the fluid sample, the sample buffer zone being positioned intermediate to the conjugate zone and the sample zone; and wherein the labeled anti-human antibody is contacted with the PF4/heparin antibodies in the fluid sample after the PF4/heparin antibodies have bound to the immobilized PF4/polyanion complex.

2. The device of claim 1, wherein the non-particulate fluorescent label is an amine-reactive dye.

3. The device of claim 1, wherein polyanion is selected from the group consisting of polyvinyl sulfonate, polystyrene sulfonate, polyanetholesulfonate, polyvinyl phosphate, polyvinyl phosphonate, polyvinyl sulfate, and a combination thereof.

4. The device of claim 3, wherein the polyanion is polyvinyl sulfonate.

5. The device of claim 1, wherein the labeled anti-human antibody is selected from the group consisting of: antibodies specific for IgG, IgA, IgM, and a combination thereof.

6. The device of claim 5, wherein the labeled anti-human antibody comprises a combination of antibodies specific for IgG, IgA, IgM.

7. The device of claim 5, wherein the labeled anti-human antibody comprises antibodies specific for IgG.

8. The device of claim 1, wherein the labeled anti-human antibody is selected from the group consisting of: a goat antibody, a donkey antibody, a horse antibody, a sheep antibody, a rabbit antibody, a mouse antibody, a rat antibody, a llama antibody, a guinea pig antibody, a hamster antibody, a chicken antibody, and a combination thereof.

9. The device of claim 1, wherein the conjugate pad further comprises a porous membrane positioned downstream of, and in fluid communication with the conjugate pad, the porous membrane comprising:
(i) a detection zone containing the PF4/polyanion complex immobilized thereon; and
(ii) a control zone containing a capture reagent immobilized thereon and configured to bind with the labeled anti-human antibody, the control zone being positioned downstream of the detection zone.

10. The device of claim 1, wherein the conjugate pad further comprises a conjugate buffer zone configured to receive a conjugate buffer, the conjugate buffer zone being positioned upstream of the conjugate zone.

11. The device of claim 1, wherein the test strip further comprises a wet pad containing a conjugate buffer zone configured to receive a conjugate buffer, the wet pad being positioned upstream of, and in fluid communication with, the conjugate pad.

* * * * *

UNITED STATES PATENT AND TRADEMARK OFFICE
CERTIFICATE OF CORRECTION

PATENT NO.        : 9,599,623 B2
APPLICATION NO.   : 14/124533
DATED             : March 21, 2017
INVENTOR(S)       : Chance et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 163 days.

Signed and Sealed this
Twenty-fifth Day of September, 2018

Andrei Iancu
*Director of the United States Patent and Trademark Office*